US009409838B2

(12) United States Patent
Schwint et al.

(10) Patent No.: US 9,409,838 B2
(45) Date of Patent: Aug. 9, 2016

(54) SELECTIVE OLEFIN EXTRACTION

(71) Applicant: Lummus Technology Inc., Bloomfield, NJ (US)

(72) Inventors: Kevin John Schwint, Long Valley, NJ (US); Robert J. Brummer, Wharton, NJ (US)

(73) Assignee: Lummus Technology Inc., Bloomfield, NJ (US)

( * ) Notice: Subject to any disclaimer, the term of this patent is extended or adjusted under 35 U.S.C. 154(b) by 430 days.

(21) Appl. No.: 14/058,607

(22) Filed: Oct. 21, 2013

(65) Prior Publication Data

US 2014/0124358 A1 May 8, 2014

Related U.S. Application Data

(60) Provisional application No. 61/723,512, filed on Nov. 7, 2012.

(51) Int. Cl.
*C07C 7/08* (2006.01)
*B01D 3/40* (2006.01)
(Continued)

(52) U.S. Cl.
CPC . *C07C 7/08* (2013.01); *C07C 7/005* (2013.01); *B01D 3/40* (2013.01); *B01D 3/4205* (2013.01); *C10G 7/08* (2013.01); *C10G 21/00* (2013.01)

(58) Field of Classification Search
CPC .......... C07C 7/08; C07C 7/005; C07C 11/08; C07C 9/10; C07C 11/00; B01D 3/40; B01D 3/4205; C10G 21/00; C10G 7/08
See application file for complete search history.

(56) References Cited

U.S. PATENT DOCUMENTS 2,415,921 A 2/1947 Wagner
3,673,081 A 6/1972 Preusser et al.
(Continued)

FOREIGN PATENT DOCUMENTS

| CN | 86104676 A | 3/1987 |
| CN | 102718618 A | 10/2012 |
| EP | 0216991 A1 | 4/1987 |
| GB | 1428228 A | 3/1976 |
| JP | 2006-092876 A | 4/2006 |

OTHER PUBLICATIONS

First Office Action issued Feb. 14, 2016 in corresponding Chinese application No. 201380060818.6 (w/translation) (16 pages).
(Continued)

*Primary Examiner* — John Kim
(74) *Attorney, Agent, or Firm* — Osha Liang LLP

(57) ABSTRACT

A process and system for separating butenes and butanes by extractive distillation using a polar solvent is disclosed. The process may include: contacting a hydrocarbon mixture including butanes and butenes with a lean solvent mixture in an extractive distillation column to form an enriched solvent fraction comprising butenes; recovering an overheads fraction comprising butanes and a bottoms fraction from the extractive distillation column; feeding the bottoms fraction to a stripper including a stripping section and a wash section; recovering the lean solvent mixture as a bottoms fraction and a stripper overheads fraction comprising butenes and water from the stripper; condensing the overheads fraction to form a water fraction and a product butenes fraction; feeding water as reflux to a top of the stripper wash section; feeding at least a portion of the condensed water fraction intermediate the top and bottom of the stripper wash section as a second reflux.

12 Claims, 3 Drawing Sheets

(51) Int. Cl.
*C07C 7/00* (2006.01)
*B01D 3/42* (2006.01)
*C10G 21/00* (2006.01)
*C10G 7/08* (2006.01)

(56) References Cited

U.S. PATENT DOCUMENTS

| | | |
|---|---|---|
| 4,556,461 A | 12/1985 | Ogura et al. |
| 5,288,370 A | 2/1994 | Asselineau et al. |
| 2005/0154246 A1 | 7/2005 | Adrian et al. |
| 2006/0096849 A1 | 5/2006 | Kerker et al. |
| 2012/0226087 A1 | 9/2012 | Kostova et al. |

OTHER PUBLICATIONS

International Search Report and Written Opinion mailed Jan. 23, 2014 in corresponding International Application No. PCT/US2013/064104 (12 pages).
Search Report and Written Opinion issued Dec. 29, 2015 in corresponding Singapore application No. 11201503484U (26 pages).
Office Action issued Apr. 1, 2016 in corresponding Canadian application No. 2,890,070 (4 pages).
Notice of Defects (Office Action) dated Apr. 13, 2016, issued by the Israeli Patent Office in related Israeli Patent Application No. 238664, with English translation (6 pages).
EPO Communication and Extended European Search Report dated Jun. 17, 2016, issued by the European Patent Office in related European Patent Application No. 13852493.9 (7 pages).

SELECTIVE OLEFIN EXTRACTION

CROSS-REFERENCE TO RELATED APPLICATIONS

This application, pursuant to 35 U.S.C. §119(e), claims priority to U.S. Provisional application Ser. No. 61/723,512, filed Nov. 7, 2012, which is herein incorporated by reference in its entirety.

FIELD OF THE DISCLOSURE

Embodiments disclosed herein relate generally to improved selective olefin extraction processes wherein condensed degasser overhead is phase separated with total aqueous phase reflux, make-up water separately refluxed, plus improved heat integration.

BACKGROUND

Butenes and butanes are products in high industrial demand and are usually obtained by working up cuts comprising $C_4$-hydrocarbons from steam or naphtha crackers. In the available raw material sources, the different isomers of the butenes and butanes and also butadiene are typically present in varying proportions. Butadiene may either be converted to n-butenes by hydrogenation or removed from these mixtures by extractive distillation. For further workup of the butenes and butanes, it is frequently necessary to separate them from each other. As a consequence of the very close proximity of their boiling points, it is generally not possible to achieve the purities required by simple distillation. As such, it is necessary to resort to other separating processes, including extractive distillation using polar solvents, such as disclosed in US20060096849.

Unfortunately, use of polar extractants, such as a mixture of N-methylpyrrolidone (NMP) and water, may result in undesirably high concentrations of water in the butene product, if not handled properly. Additionally, use of such mixtures adds the potential for formation of separate hydrocarbon and aqueous phases on trays or packing in a tower, which may reduce the separation efficiency of the tower.

SUMMARY OF THE CLAIMED EMBODIMENTS

In one aspect, embodiments disclosed herein relate to a process for separating butenes and butanes by extractive distillation using a polar solvent. The process may include: contacting a hydrocarbon mixture comprising butanes and butenes with a lean solvent mixture comprising water and one or more polar solvents in an extractive distillation column to form an enriched solvent fraction comprising the butenes and solvent(s); recovering an overheads fraction comprising butanes from the extractive distillation column; recovering the enriched solvent fraction as a bottoms fraction from the extractive distillation column; feeding the bottoms fraction to a stripper comprising a stripping section and a wash section to separate the butenes from the solvent mixture; recovering the lean solvent mixture as a bottoms fraction from the stripper; recovering a stripper overheads fraction comprising butenes and water from the stripper; condensing the overheads fraction to form a water fraction and a product butenes fraction; feeding water as a reflux to a top of the stripper wash section; feeding at least a portion of the condensed water fraction intermediate the top and bottom of the stripper wash section as a second reflux.

In another aspect, embodiments disclosed herein relate to a system for separating butenes and butanes by extractive distillation using a polar solvent. The system may include: an extractive distillation column for contacting a hydrocarbon mixture comprising butanes and butenes with a lean solvent mixture comprising water and one or more polar solvents to recover an enriched solvent fraction comprising the butenes and solvent(s) as a bottoms fraction and to recover an overheads fraction comprising the butanes; a stripper comprising a lower stripping section and an upper wash section to separate the bottoms fraction and recover an overheads fraction comprising butenes and water and a bottoms fraction comprising the lean solvent mixture; a stripper overheads system for condensing the overheads fraction to form a water fraction and a product butenes fraction; a flow conduit for feeding water as a reflux to a top of the stripper wash section; a flow conduit for feeding at least a portion of the condensed water fraction intermediate the top and bottom of the stripper wash section as a second reflux.

Other aspects and advantages will be apparent from the following description and the appended claims.

DETAILED DESCRIPTION

In one aspect, embodiments herein relate to a process for separating butenes and butanes from a stream comprising a mixture of $C_4$-hydrocarbons by extractive distillation using a polar extractant. Polar extractants according to embodiments disclosed herein may include, for example, dimethylformamide (DMF), N-methylpyrrolidone (NMP), acetonitrile, furfural, N-formylmorpholine, and dimethylacetamide. The extractants may be used either anhydrously or virtually anhydrously or in a mixture of from 0.1 to 20% by weight water. In another aspect, embodiments disclosed herein relate to selective olefin extraction processes wherein condensed degasser overhead is phase separated with total aqueous phase reflux and make-up water separately refluxed, thereby avoiding formation of two liquid phases within the columns and improving product separation efficiency. Embodiments disclosed herein also provide improved heat integration. Each of these aspects are described in more detail below with respect to FIGS. 1 and 2.

Figure 1:
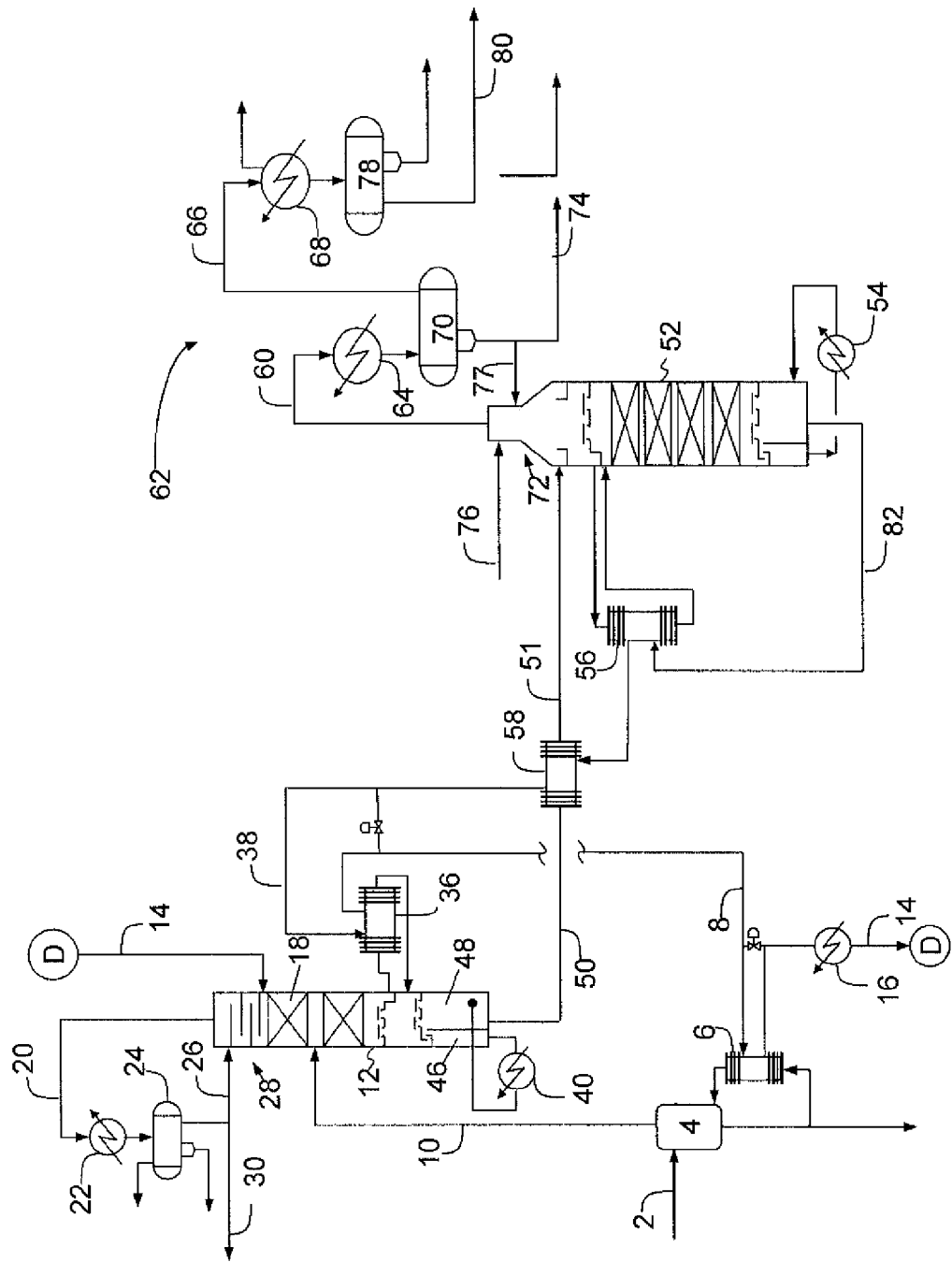
FIG. 1 is a simplified flow diagram of a process for separating butenes from butane according to embodiments disclosed herein.

Referring now to FIG. 1, a simplified flow diagram of a process for separating butenes from butane according to embodiments disclosed herein is illustrated. A mixture of butanes and butenes, such as a mixed C4 fraction or a raffinate-1 from a butadiene extraction unit, is fed via flow line 2 to feed vaporization drum 4 and vaporized in the feed vaporizer 6, which may be a thermosyphon exchanger. Feed vaporizer 6 utilizes hot lean solvent 8 as the heating medium. If the overhead fraction from the main washer of a butadiene extraction unit (not shown) is taken directly, a feed vaporizer would not be required.

Vaporized feed 10 is introduced to the middle of butene absorber 12. Lean solvent 14, cooled in the solvent cooler 16, is fed above the top bed 18 of the butene absorber 12, where butenes are selectively absorbed and less soluble butanes travel up the column and are collected as an overheads fraction 20. Overhead fraction 20 is condensed in condenser 22 against cooling water, and the condensed butanes are collected in the drum 24. A portion of the condensed butanes are fed via flow line 26 as reflux to wash trays 28 at the top of the butene absorber 12, which serve to knock down entrained solvent. The balance of the butane distillate is recovered as butane product 30.

Figure 2:
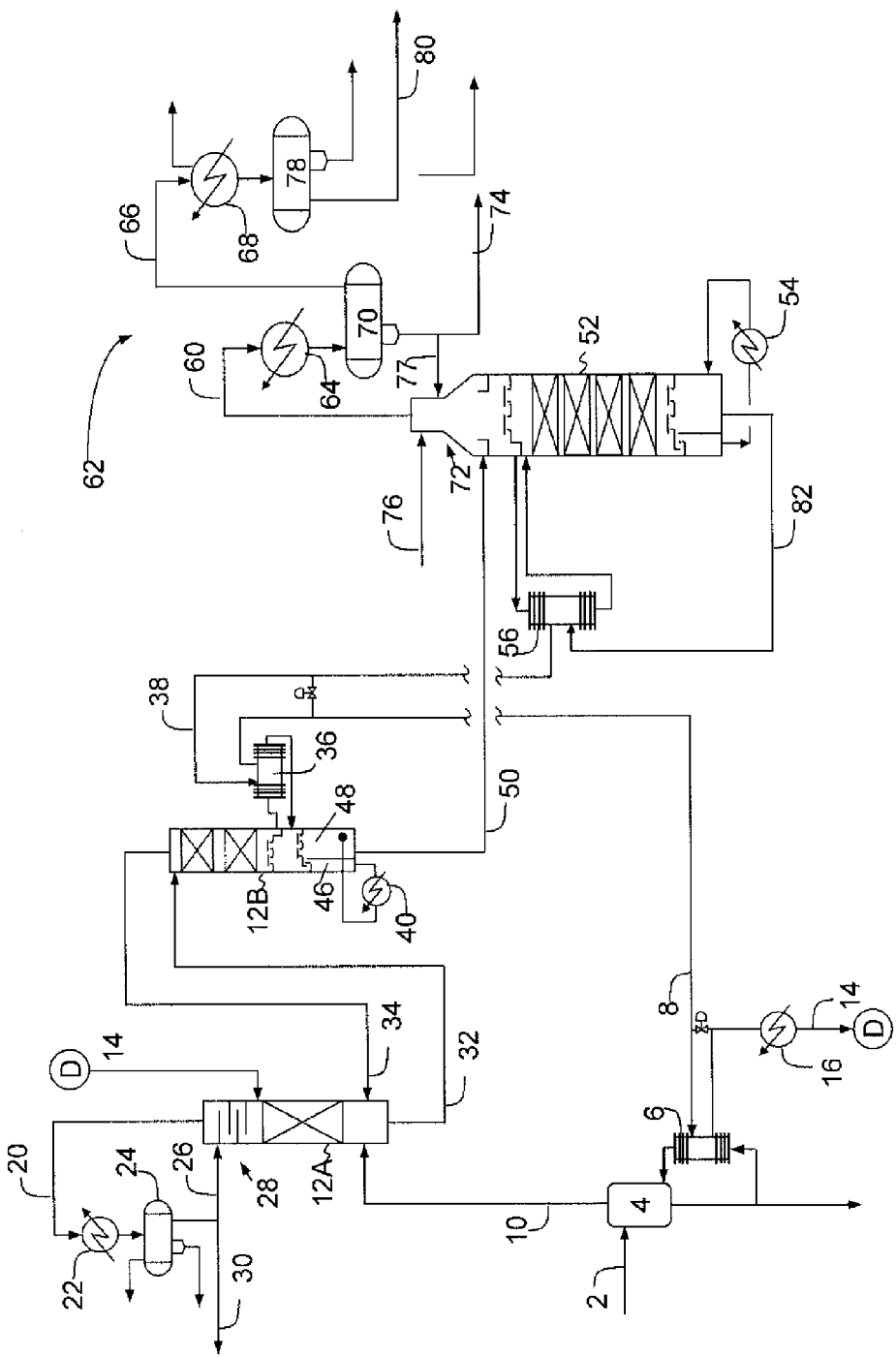
FIG. 2 is a simplified flow diagram of a process for separating butenes from butane according to embodiments disclosed herein.

In some embodiments, a two column system Butene Absorber/Butene Rectifier system extractive distillation system may be necessary, such as where very tight butane and very tight butene specifications are both required. In such a case, a two column system may be necessary due to the increased number of stages required and column height limitations. Referring now to FIG. 2, where like numerals represent like parts, in this embodiment the vaporized feed 10 is introduced to the bottom of the butene absorber 12A. The bottoms 32 of the Butene Absorber are pumped to the top of the butene rectifier 12B, and the butene rectifier overhead 34 flows by pressure difference to the bottom of butene absorber 12A. Hence, the butene rectifier 12B is just an extension of the butene absorber 12A, but built as a separate column; the two columns operate similar to that of butene absorber 12, with additional staging and height to meet the heightened separation specifications.

Referring now to FIGS. 1 and 2, the butene absorber bottoms are reboiled in one or more butene absorber side reboilers 36, utilizing hot lean solvent 38 as the heating medium. All side reboilers 36 may be once-thru vaporizing type reboilers. For very tight butene and butane specifications, a butene absorber reboiler 40 may be required, using tempered water or steam as a heat exchange medium.

The extractive of butenes with solvent/water in butene absorber/rectifier 12 may be carried out at a pressure in the range from about 2 bar to about 15 bar and at temperatures in the range from about 40° C. to about 100° C.

Figure 3:
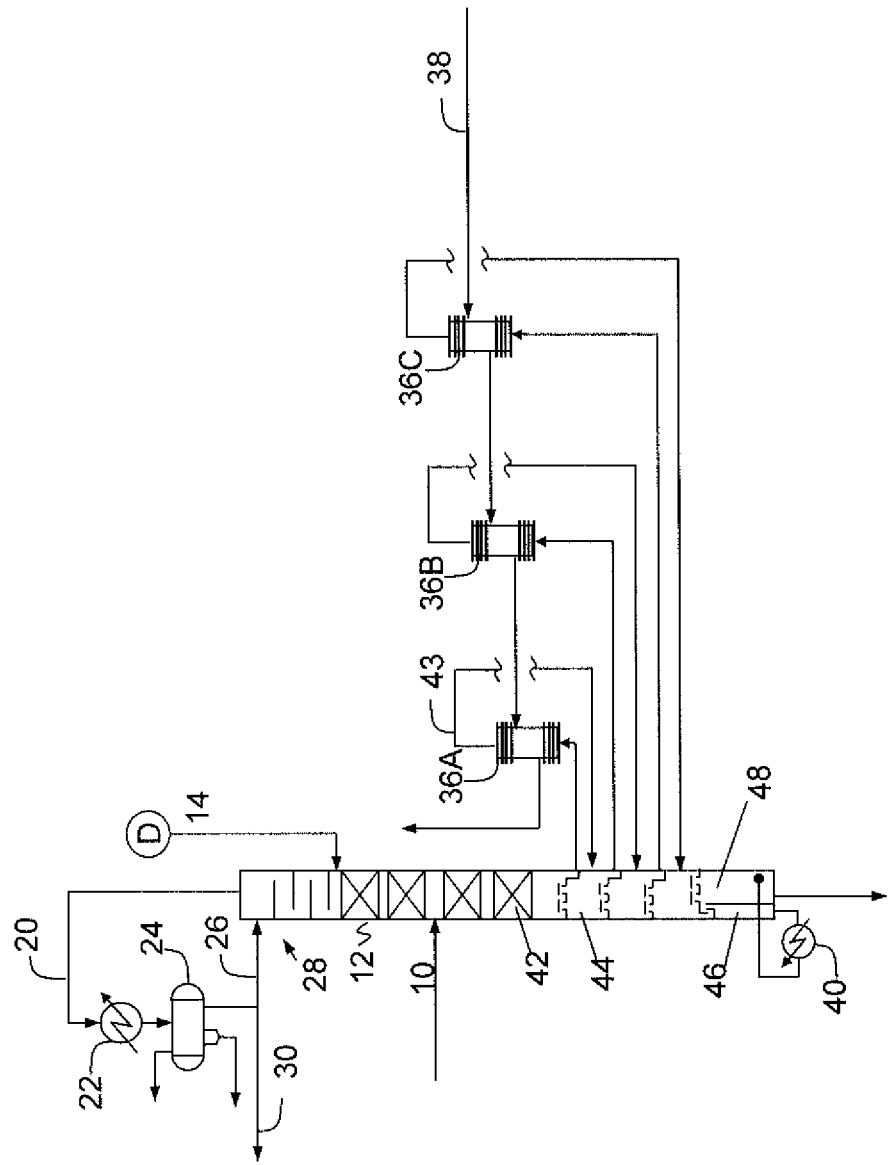
FIG. 3 is a simplified flow diagram of a process for separating butenes from butane according to embodiments disclosed herein.

In some embodiments, a series of counter-current reboilers, including two, three, four, or more butene absorber side reboilers 36 may be provided, where liquid fractions withdrawn from higher up the column (i.e., lower temperature fractions) are heated using hot lean solvent discharged from lower side reboilers (i.e., higher temperature fractions). For example, as shown in FIG. 3, liquid from the bottom bed 42 of butene absorber 12 is collected in a chimney tray and fed to reboiler 36A. The mixed phase reboiler outlet 43 is returned to butene absorber 12 into a compartment 44 below where the reboiler inlet is withdrawn. The vapor and liquid phases are separated in compartment 44, where the liquid phase is collected on a lower chimney tray and fed to reboiler 36B, and the vapor passes through the chimney tray above and enters the bottom bed 42 of the butene absorber. As illustrated, there are three counter-current series flow reboilers 36 (A, B, C) that interchange heat with the lean solvent 38 and operate in a similar fashion (liquid draw, with mixed phase returned below draw tray). Liquid from the reboiler 36C is collected in a baffled compartment 46 at the bottom of butene absorber 12 and fed to reboiler 40, which may use steam as a heating fluid. Reboiler 40 may also be a once-thru vaporizing type reboiler, using low pressure (LP) steam as the heating medium instead of hot lean solvent. The LP steam provides a portion of the net heat input into the system, and is utilized for control purposes. The outlet of the butene rectifier steam reboiler 40 is separated in the bottom of the column 12 and the liquid is collected in the column sump 48. In the case where butane and/or butene product specifications are loose, the steam reboiler may not be required. In the case where butane and butene product specifications are tight, medium pressure (MP) steam may be required.

The use of once-thru vaporizing reboilers may allow greater heat removal from the lean solvent than by suppressed vaporization type reboilers. Additionally, as fouling is not an issue, suppressed vaporization type reboilers are not required. With vaporizing type reboilers, however, the cold side temperate rise is lower than with suppressed vaporization type reboilers, and thus the mean temperature difference is greater. For the embodiment illustrated in FIG. 3, reboilers 36A, 36B, and 36C may be configured for counter-current flow and may be designed for a 10° C. outlet temperature approach (i.e., hot outlet temperature minus cold outlet temperature=10° C.) in order to maximize heat recovery while keeping surface area to a minimum.

The combination of solvent flow into column 12 and reboiler heat affect the separation of butanes and butenes in the butene absorber, as described above, resulting in the desired extractive distillation. Rich solvent from sump 48 is then pumped via flow line 40 to the top of butene stripper 52, where dissolved butenes are removed from the rich solvent. In some embodiments, the butene absorber bottoms pump (not illustrated) may be omitted, such as where the pressure difference between the absorber 12 and stripper 52 is sufficient to effect the desired transfer of fluid. This will, of course, also depend on the utilities available, required product specifications, and other design considerations.

Stripping heat is proved by the butene stripper steam reboiler 54 utilizing MP steam as the heating medium, and the butene stripper side reboiler 56 utilizing butene stripper bottoms (hot lean solvent) as the heating medium. Both reboilers 54, 56 may be counter-current, once-thru vaporizing type reboilers, for similar reasons as discussed above, as well as the fact that use of a side stream vaporizing reboiler is more efficient than a suppressed vaporization type feed heater (feed/effluent exchanger) typically used. As noted above, the vaporizing type reboiler has a lower temperature rise than a suppressed vaporization type reboiler, and this provides the benefits already discussed. Further, to add additional heat into the butene absorber bottoms 50/51, which may be at its bubble point, would require an additional pump to provide the pressure necessary to suppress vaporization. In embodiments where butane and butene product specifications are loose, an additional butene stripper side reboiler in series (not shown), or alternatively a feed/effluent exchanger 58, as shown in FIG. 1, may be required.

The butene stripper 52 bottoms fraction, hot lean solvent fraction 82, may be recirculated back to column 12 and used as a heat exchange medium as described above. The butene stripper 52 overhead fraction 60 is condensed in a two stage condensing system 62. In the first stage, the overhead fraction 60 is cooled to approximately 60° C. in the butene stripper main condenser 64, where essentially all of the water and no hydrocarbons are condensed. The butene stripper main condenser 64 can be an air cooled or water cooled condenser, depending on plant economics and/or cooling water availability. In the second stage, the un-condensed vapor 66, including essentially all of the product butenes, is cooled down to approximately 40° C. in the butene product condenser 68, where essentially all of the hydrocarbons and little or no water are condensed. Butene product condenser 68 may be a water cooled condenser.

Water condensed in the butene stripper main condenser 64 is collected in the butene stripper reflux drum 70 and pumped back to a mid-point in the wash tray section 72 of butene stripper 52. A portion of the condensed water can be purged to a waste water stripper (not shown) via flow line 74 for removal of intermediate boiling impurities, if necessary.

Cooled, clean steam condensate 76, which is required to make up for water losses from the system, is refluxed to the top most wash tray of butene stripper 52. The trays between clean water reflux 76 inlet (top of wash trays) and the condensed water reflux 77 (recycle water) inlet (at approximately the mid-point of the wash tray section 72) provide additional washing of solvent from the overhead fraction. Butenes condensed in the butene stripper product condenser 68 are collected in butene product drum 78 and pumped to product storage via flow line 80.

The separation of butenes from solvent/water in stripper 52 may be carried out at a pressure in the range from about 0.5 bar to about 7 bar, such as from about 1 bar to about 3 bar. In accordance with this pressure, the temperatures may vary from about 100° C. to about 220° C., such as from about 125° C. to about 160° C.

As described above, clean condensate is refluxed to the top of butene stripper 52. By refluxing only water to the top of stripper 52, a continuous aqueous phase forms on all the wash trays above the rich solvent feed point. Hydrocarbons, stripped from the rich solvent, travel up the column as vapor without condensing and without forming a separate hydrocarbon phase on the wash trays. The loss of separation efficiency, which would have resulted from having two separate liquid phases, is therefore avoided.

The majority of the water contained in the stripper overheads fraction 60 can be condensed at a significantly higher temperature than that required to condense the product butenes. Accordingly, a two stage stripper overhead condensing system can be advantageously employed. In the first stage, essentially all of the water and no hydrocarbons are condensed; and in the second stage, essentially all of the hydrocarbons and no water are condensed. In the first stage, the condensing temperature may be in the range from about 50° C. to about 70° C., such as about 60° C., and in the second stage, the condensing temperature may be in the range from about 30° C. to about 45° C., such as about 38° C. The two stage condensing system makes the water—hydrocarbon separation much more efficient. It also allows the optional use of an air cooler in the first stage, which can be more economical at some locations. Lastly, the water only has to be cooled down to its bubble point (~60° C.) and not down to the bubble point of the product butenes (~38° C.). This is more energy efficient and saves cooling water utilities.

Because hydrocarbons are not refluxed to the top of stripper 52, the tray loading of the wash trays in zone 72 are significantly reduced. Accordingly, the diameter of wash tray section 72 of stripper 52 can be reduced. Furthermore, the heat duty of stripper 52 is reduced as there are no refluxed hydrocarbons that need to be re-vaporized (other than a minor quantity of hydrocarbons dissolved in the aqueous phase).

Water make-up may be added to the process via reflux line 72 to compensate for any dissolved water exiting with the butane and butene products, and water purge 74. The water make-up is in the form of cooled, clean steam condensate, which contains no solvent. This puts clean water to the best use by having it contribute to the fractionation of solvent from water, instead of simply mixing it with lean solvent (or solvent and water), as is common in other processes for the separation of butenes from butane.

Additionally, as described above, heat integration between the hot lean solvent and other process streams is greatly improved. First, degasser 52 bottoms are interchanged with a side reboiler 56 on the degasser 52. This adds heat lower in the degasser than with only a feed/effluent exchanger. Second, the degasser bottoms 82 partially cooled in the degasser side reboiler 56 may be interchanged with absorber bottoms in a series of reboilers 36. This allows greater heat removal (heat recovery) from the lean solvent than by a single suppressed vaporization type reboiler.

Advantageously, the processes for separating butenes from butanes as described above addresses the problem of separate liquid phases that form at the top of the stripper. The decline in separation efficiency that would be a result of separate liquid phases is therefore avoided. Additionally, make-up water is introduced at the optimal point in the process. The introduction of make-up water at the top of the stripper, instead of into the lean solvent recycle stream, enhances the separation of solvent from the butene product. Further, embodiments disclosed herein are highly energy efficient; the utilization of the enthalpy of the lean solvent recycle may be maximized.

As a further advantage, several wash trays (such as about 10-15) are used above the stripper stages (packed beds), where the entire stripper overheads are washed with condensed water/solvent. Butenes are not refluxed back to the stripper. As a result, the amount of solvent in the stripper overheads and in the water reflux is greatly reduced. For example, embodiments disclosed herein may have less than 10 ppm by weight solvent, and 5 ppm solvent or less in some embodiments, in the stripper overheads; additionally, embodiments disclosed herein may have less than 1 ppm by weight solvent in the butenes product. This results in a superior butenes product as well as less solvent losses. Embodiments disclosed herein may also have a lower solvent to feed ratio as compared to typical butane/butene separation processes. As a result of the improved tray efficiency of the stripper wash trays, improved overall absorption and stripping efficiency, improved heat integration and energy recovery, and lower solvent rate, processes according to embodiments disclosed herein may have lower operating expenses and lower capital costs as compared to prior butane/butene separation schemes.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for separating butenes and butanes by extractive distillation using a polar solvent, the process comprising:

contacting a hydrocarbon mixture comprising butanes and butenes with a lean solvent mixture comprising water and one or more polar solvents in an extractive distillation column to form an enriched solvent fraction comprising the butenes and solvent(s);

recovering an overheads fraction comprising butanes from the extractive distillation column;

recovering the enriched solvent fraction as a bottoms fraction from the extractive distillation column;

feeding the bottoms fraction to a stripper above a stripping section and below a wash section of the stripper to separate the butenes from the enriched solvent fraction;

recovering the lean solvent mixture as a bottoms fraction from the stripper;

recovering a stripper overheads fraction comprising butenes and water from the stripper;

condensing the stripper overheads fraction to form a condensed water fraction and a product butenes fraction;

feeding water as a reflux to a top of the stripper wash section;

feeding at least a portion of the condensed water fraction intermediate the top and bottom of the stripper wash section as a second reflux.

2. The process of claim 1, wherein the hydrocarbon mixture is a vapor fraction recovered from a butadiene recovery process.

3. The process of claim 1, further comprising vaporizing the hydrocarbon mixture in a feed vaporization system prior to the contacting.

4. The process of claim 1, wherein the condensed water fraction used as the second reflux is a single liquid phase.

5. The process of claim 1, wherein the condensing the stripper overheads fraction comprises condensing the stripper overheads fraction in a two-stage condensation process comprising:
    partially condensing the stripper overheads fraction to condense and recover the water as the condensed water fraction and to recover a vapor fraction comprising the butenes;
    condensing the vapor fraction comprising the butenes to form the product butene fraction.

6. The process of claim 1, wherein the stripper overheads fraction comprises less than 10 ppm solvent, by weight.

7. The process of claim 1, wherein the stripper overheads fraction comprises 5 ppm or less solvent, by weight.

8. The process of claim 1, wherein the product butene fraction comprises less than 1 ppm solvent, by weight.

9. The process of claim 1, further comprising:
withdrawing a liquid side draw from the stripper;
at least partially vaporizing the liquid side draw by indirect heat exchange in a first heat exchanger with the lean solvent mixture recovered as a bottoms fraction from the stripper;
returning the at least partially vaporized side draw to the stripper.

10. The process of claim 9, further comprising:
recovering a partially cooled lean solvent mixture from the first heat exchanger;
contacting at least one of (a) the enriched solvent fraction as a bottoms fraction from the extractive distillation column and (b) one or more liquid side draws from the extractive distillation column via indirect heat exchange in a second heat exchanger with the partially cooled lean solvent mixture.

11. The process of claim 10, wherein at least one of the first heat exchanger and the second heat exchanger is a once-thru vaporization type exchanger.

12. The process of claim 10, further comprising contacting a partially cooled lean solvent mixture recovered from at least one of the first heat exchanger and the second heat exchanger via indirect heat exchange with the hydrocarbon mixture to at least partially vaporize the hydrocarbon mixture prior to the contacting.

* * * * *